(12) United States Patent
Vismans et al.

(10) Patent No.: US 9,573,877 B2
(45) Date of Patent: Feb. 21, 2017

(54) PROCESS FOR PRODUCING VINYL ACETATE

(71) Applicant: Celanese International Corporation, Irving, TX (US)

(72) Inventors: Pieter Vismans, Houston, TX (US); Naveed Aslam, Houston, TX (US); Tony Hammock, League City, TX (US); Kevin Hanks, League City, TX (US); Ilias S. Kotsianis, Houston, TX (US); Tianshu Pan, Houston, TX (US); Daniel Rangel-Osalde, League City, TX (US); Kelly Wallace, Baytown, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 123 days.

(21) Appl. No.: 13/975,552

(22) Filed: Aug. 26, 2013

(65) Prior Publication Data

US 2014/0066649 A1 Mar. 6, 2014

Related U.S. Application Data

(60) Provisional application No. 61/697,611, filed on Sep. 6, 2012.

(51) Int. Cl.
*C07C 67/05* (2006.01)
*C07C 67/055* (2006.01)

(52) U.S. Cl.
CPC ............ *C07C 67/05* (2013.01); *C07C 67/055* (2013.01)

(58) Field of Classification Search
CPC .................. C07C 67/05; C07C 69/15
See application file for complete search history.

(56) References Cited

U.S. PATENT DOCUMENTS

| 3,855,280 | A | * | 12/1974 | Severs, Jr. ............ C07C 67/055 560/243 |
| 5,952,523 | A | | 9/1999 | Papavassiliou et al. |
| 6,342,628 | B1 | | 1/2002 | Williams et al. |
| 6,420,595 | B1 | * | 7/2002 | Hallinan et al. ............. 560/245 |
| 2014/0303398 | A1 | | 10/2014 | Zhang et al. |

FOREIGN PATENT DOCUMENTS

| CN | 102381966 A | 3/2012 |
| EP | 0845453 | 6/1998 |
| EP | 0845453 A2 * | 6/1998 |
| EP | 1 006 100 A1 | 6/2000 |
| GB | 1146731 | 3/1969 |

OTHER PUBLICATIONS

Luyben, Industrial & Engineering Chemical Research, Design and Control of a Modified Vinyl Acetate Monomer Process, 2011, 50 pp. 10136-10147.*
Delugogorski et al, Halon Options Technical Working Conference, Water Vapor as an Inerting Agent, 1997, pp. 7-18.*
International Search Report and Written Opinion for PCT/US2013/056598 mailed Jan. 22, 2014.

* cited by examiner

*Primary Examiner* — Paul A Zucker
(74) *Attorney, Agent, or Firm* — Kilpatrick Townsend & Stockton LLP (57) ABSTRACT

The present invention relates to a process for forming vinyl acetate. The process comprises the step of providing a reaction mixture having an initial heat capacity. The reaction mixture comprises acetic acid, oxygen, ethylene, and optionally water. The process further comprises the step of adding to the reaction mixture at least one heat capacity modifier to form an increased heat capacity reaction mixture. The process further comprises the step of contacting the acetic acid, oxygen, and ethylene over a catalyst under conditions effective to form a crude vinyl acetate product. The crude vinyl acetate product comprises vinyl acetate and water.

16 Claims, 2 Drawing Sheets

PROCESS FOR PRODUCING VINYL ACETATE

CROSS REFERENCE TO RELATED APPLICATIONS

This is a non-provisional which claims priority to U.S. Provisional Application No. 61/697,611 filed on Sep. 6, 2012, the entirety of which is hereby incorporated by reference.

FIELD OF THE INVENTION

The present invention relates to processes for producing vinyl acetate and, in particular, to process control techniques that, when used in vinyl acetate processes, provide for improvements in reaction efficiencies.

BACKGROUND OF THE INVENTION

Vinyl acetate is conventionally produced via a vapor phase reaction of ethylene, oxygen and acetic acid, e.g., the acetoxylation of ethylene. The reaction is typically conducted in a fixed bed catalyst reactor. The catalyst may comprise palladium or a palladium/gold mixture, which is supported on a silica or alumina base. In addition to the formation of vinyl acetate, the undesired combustion of ethylene to form carbon dioxide and water also takes place. Other undesired impurities that may be formed include acetaldehyde, ethyl acetate, methyl acetate, acetone, ethylene glycol diacetate, acrolein and crotonaldehyde.

The selectivity and conversion relating to the reaction are functions of several variables including reactor temperature, component concentration, and the condition of the catalyst. Deactivation of the catalyst, which routinely occurs over time due to buildup of tars and polymeric materials on the catalyst surface and/or to structural changes of the catalyst metals, can adversely affect the reaction process, particularly with regard to selectivity. These changes in reactor performance can ultimately lead to compositional changes in the liquid stream entering the purification section of a vinyl acetate plant.

The reaction yields a crude vinyl acetate product comprising vinyl acetate, water, and carbon dioxide as well as unreacted ethylene and acetic acid, which are used in excess. The ethylene and acetic acid are recycled back to the reactor from the reaction and purification sections of the unit. Product vinyl acetate is recovered and purified in the purification section and sent to storage tanks. Wastewater is sent to a treatment facility and carbon dioxide is vented to a pollution control device. Inert gases such as nitrogen and argon may accumulate over time and may then be purged from the reaction section to minimize buildup.

Generally speaking, the rate of acetoxylation increases as the concentration of oxygen in the reactor is increased. However, the amount of oxygen that may be introduced into the reactor is limited by a flammability limit of the reaction mixture. The flammability limit is typically defined as the lowest concentration of oxygen in a mixture that will result in a pressure rise when it contacts an ignition source. If the oxygen concentration exceeds this flammability limit, a fire or explosion could result.

Various steps have been taken to minimize the risk of such a fire or explosion. For example, in the fixed-bed reactor of EP 0 845 453, the concentration of oxygen in the inlet gas composition is closely monitored and maintained at or near a threshold value. The mathematical approximations used to define this threshold value are described in EP 0 845 453 which is incorporated herein by reference. When the inlet oxygen concentration exceeds this threshold value, a shutdown signal is activated, and the reaction is quenched by shutting off the ingress of fresh oxygen into the reactor.

The conventional calculation of flammability limits and/or the establishment of non-flammability ranges, however, may be inherently inaccurate. The conventional experimental techniques and methods that are used to develop mathematical correlations generally calculate flammability limits that are low. These correlations provide a buffer from the true flammability limit. Although safety is achieved, reaction efficiencies suffer due to operation at lower oxygen concentrations.

Even in view of the conventional processes, the need exists for a vinyl acetate production process that calculates more accurate flammability limit correlations, which provide for safe control of the process and improved operational efficiencies.

The references mentioned herein are hereby incorporated by reference.

SUMMARY OF THE INVENTION

The present invention, in one embodiment, relates to a process for forming vinyl acetate. The process comprises the step of providing a reaction mixture. The reaction mixture has an initial heat capacity and comprises acetic acid, oxygen, ethylene, and optionally water. The process may further comprise the step of increasing the heat capacity of the reaction mixture. Preferably this step is achieved by adding to the reaction mixture at least one heat capacity modifier to form an increased heat capacity reaction mixture. The process further comprises the step of contacting the acetic acid, oxygen, and ethylene over a catalyst under conditions effective to form a crude vinyl acetate product comprising vinyl acetate and water. In one embodiment, at least one component of the reaction mixture, e.g., the acetic acid, is vaporized before being added to the reaction mixture. Preferably, the reaction mixture comprises at least 1 mol % of at least one heat capacity modifier and from 20 mol % to 70 mol % ethylene.

In one embodiment, the process comprises the step of contacting acetic acid, oxygen, ethylene in the presence of water and over a catalyst under conditions effective to form a crude vinyl acetate product comprising, inter alia, vinyl acetate and water. The inventive process further comprises the step of calculating a flammability limit based on water content in the reaction mixture. Preferably, the water content in the reaction mixture is calculated based on water content of a derivative stream, which is formed from the crude vinyl acetate product. In one embodiment, the water content of the derivative stream is measured via an infrared analyzer. The process further comprises the step of adjusting a reaction parameter based on the flammability limit.

BRIEF DESCRIPTION OF DRAWINGS

The invention is described in detail below with reference to the appended drawings, wherein like numerals designate similar parts.

DETAILED DESCRIPTION OF THE INVENTION

Introduction

Vinyl acetate is typically produced via the continuous vapor phase acetoxylation reaction of ethylene. This reaction is usually conducted in a fixed bed catalyst reactor. The acetoxylation rate generally increases as the concentration of oxygen in the reactor is increased. However, the amount of oxygen that may be introduced into the reactor is limited by a flammability limit of the reaction mixture, which typically is defined as the lowest concentration of oxygen in a mixture that will provide for combustion, e.g., result in a pressure rise when ignited. The flammability limits are usually calculated using mathematical formulae. The conventional calculation of these flammability limits and/or the establishment of non-flammability ranges, however, may be inherently inaccurate. Often, the calculated flammability limits are too low. As a result, although a high level of safety is achieved, the reaction is required to be conducted within non-flammability ranges that are lower than necessary, e.g., levels below the inaccurate flammability limits. Accordingly, when using conventionally calculated flammability limits, lower oxygen concentrations must be employed and reaction efficiencies suffer.

It has now been discovered that surprisingly and unexpectedly when the calculation of the flammability limit is based on, inter alia, the water content of the reaction mixture, the calculated flammability limit more accurately estimates the true flammability limit of the reaction mixture when the reaction mixture is reacted in accordance with the invention. Conventional vinyl acetate control processes fail to take into consideration the effects of water in the reaction mixture and the effects that this water may have on the thermodynamics of the reaction mixture, e.g., the flammability limit. As a result, conventionally calculated flammability limits may be lower than are actually necessary. Although this may provide extremely safe operating conditions, reaction productivity suffers. Without being bound by theory, water contained in the reaction mixture may interact with the acetic acid in the vapor phase, which may affect the true flammability limit of the reaction mixture. Thus, by taking into effect the water content of reaction mixture, a more accurate calculation of the flammability limit may be achieved. As a result of the inventive calculated flammability limits, the vinyl acetate process is capable of operating at higher oxygen concentrations, which leads to several benefits. For example, with the higher oxygen concentrations, oxygen conversion can be reduced, which leads to decreases in unwanted by-products, e.g., carbon dioxide, selectivity and/or increases in vinyl acetate selectivity while maintaining ethylene conversion. The lower oxygen conversions may be achieved by reducing the reactor temperature, which also provides a safety benefit. As another advantage, if oxygen conversions are maintained at typical levels, the higher oxygen concentrations will lead to higher vinyl acetate yields.

Also, conventional control processes typically adjust the reaction parameters, e.g., reactant concentration or reactor temperature, to maintain the oxygen concentration below the respective flammability limits. For example, the flow rate of a solution stream in a transfer line can be increased or decreased going into or out of a column to alter the concentration of one or more of the components in that column or another vessel in the reaction system. Alternatively, the temperature of the solution in a column or stream or the temperature profile or gradient in a column could be increased or decreased to affect the concentration of one or more components in the reaction system solution. Also, the concentration of a reaction system component can be adjusted by direct addition or extraction of that component into or out of the solution. These techniques may be effective in maintaining the oxygen concentration.

It has also been discovered that by varying, e.g., reducing, the heat capacity of the reaction mixture prior to reaction, improved reaction efficiencies surprisingly and unexpectedly can be achieved. Preferably the variance of the heat capacity is achieved by adding to the reaction mixture at least one heat capacity modifier. "Heat capacity modifier" in the context of this application means that a compound, other than the reactants such as ethylene, oxygen, and acetic acid, that does not react under ethylene acetoxylation conditions. Heat capacity modifiers, in some embodiments, include inert compounds, e.g., nitrogen. However, other compounds not conventionally known as inerts may also be considered to be a heat capacity modifier in this context. Because the heat capacity of the reaction mixture is reduced, the vinyl acetate formation reaction, advantageously, may run at higher oxygen concentrations.

Accordingly, the present invention relates to a process for producing vinyl acetate. In one embodiment, the processes comprise the step of contacting acetic acid, oxygen, ethylene in the presence of water and over a catalyst under conditions effective to form a crude vinyl acetate product comprising vinyl acetate and water. The inventive process further comprises the step of calculating a flammability limit based on, inter alia, water content in the reaction mixture. In one embodiment, the content of other organic and/or inert compounds also may be utilized in the flammability limit calculation. As noted above, when the flammability limit is calculated in this manner, the calculated flammability limit more accurately reflects the actual flammability limit of the reaction mixture, as opposed to conventional calculations, which do not consider water content.

In preferred embodiments, the water content in the reaction mixture is calculated based on water content of a derivative stream. The water content of the derivative stream may be related to the water content of the reaction mixture. In one embodiment, the process comprises the step of forming a derivative stream from the crude vinyl acetate product and measuring the water content thereof. In some of these embodiments, the measurement of the water content of the derivative stream, e.g., the liquid distillation residue, provides an accurate measurement of the actual vapor reaction mixture. In some cases, the actual water content of the reaction mixture may be difficult to accurately measure due to, for example, the thermodynamics of the reaction mixture, which is a high temperature/high pressure vapor. In one embodiment, the water content of the reaction mixture is measured directly from the reaction mixture. The measurement of the water content of the derivative stream, in accordance with the present invention, beneficially provides an accurate measurement of the water content in the reaction mixture. The derivative stream may comprise water and optionally acetic acid. The derivative stream, in one embodiment, may be a stream that is directly or indirectly recycled to the reactor. Preferably, the derivative stream is formed by a column in a separation zone. For example, the derivative stream may be a residue of a distillation column, e.g., an azeotropic distillation column. Preferably, the water content of the derivative stream is measured via an infrared analyzer.

The processes further comprise the step of adjusting reaction parameters based on the calculated flammability limit. Preferably, the adjusting step comprises adjusting the oxygen concentration based on the calculated flammability limit. Because the calculated flammability limit is more accurate, the process can be adjusted to run at more efficient conditions, e.g., closer to the actual flammability limit. Because the ethylene acetoxylation has the ability to run at higher oxygen concentrations, high ethylene efficiency is achieved.

The ethylene acetoxylation and the accompanying side reactions also produce impurities such as carbon monoxide. Surprisingly and unexpectedly, the inventive vinyl acetate process provides for high ethylene conversions, which are accompanied by decreases in impurity selectivity, e.g., carbon monoxide selectivity. In one embodiment, ethylene conversion is at least 5%, e.g., at least 10% or at least 15%. In terms of ranges, ethylene conversion may range from 5% to 35%, e.g., from 7% to 30% or from 10% to 20%. In terms of upper limits, ethylene conversion may be less than 35%, e.g., less than 30% or less than 20%. Preferably, carbon dioxide selectivity build ranges around 8 is less than 25%, e.g., less than 20% or less than 15%. In terms of ranges, carbon dioxide selectivity may range from 0.1% to 25%, e.g., from 1% to 20% or from 3% to 15%. The inventive process beneficially achieves a high vinyl acetate selectivity. In one embodiment, vinyl acetate selectivity is at least 65%, e.g., at least 75% or at least 85%. In terms of ranges, vinyl acetate selectivity may range from 65% to 99%, e.g., from 75% to 95% or from 85% to 92%.

Regarding the inventive heat capacity reduction, the inventive process comprises the step of providing a reaction mixture comprising acetic acid, oxygen, ethylene, and optionally water. The reaction mixture may have an initial heat capacity. The process further comprises the step of increasing the heat capacity of the reaction mixture. Preferably this step is achieved by adding to the reaction mixture at least one heat capacity modifier. In a preferred embodiment, the heat capacity modifier(s) comprise methane, although any suitable heat capacity modifier(s) may be employed. For example, the heat capacity modifier(s) may be selected from the group consisting of nitrogen, water, ethane, carbon dioxide, and mixtures thereof. Upon the addition of the heat capacity modifier(s) the heat capacity of the reaction mixture is increased. As discussed above, the heat capacity modifiers of the present invention, in some embodiments, exclude the reactants of the ethylene acetoxylation reaction.

The processes further comprise the step of contacting the acetic acid, oxygen, and ethylene over a catalyst under conditions effective to form a crude vinyl acetate product comprising vinyl acetate and water. In one embodiment, at least one component of the reaction mixture, e.g., the acetic acid, is vaporized before being added to the reaction mixture. In one embodiment, the at least one component of the reaction mixture is provided as a vapor and does not require vaporization. Because the heat capacity of the reaction mixture is increased, the reaction mixture can utilize a higher oxygen content without the flammability concerns typically associated therewith.

In one embodiment, the combined reactants in the increased heat capacity reaction mixture comprise at least 1 mol % of heat capacity modifier(s), e.g., at least 5 mol % or at least 10 mol %. In terms of ranges, the increased heat capacity reaction mixture may comprise from 1 mol % to 50 mol % heat capacity modifier(s), e.g., from 5 mol % to 40 mol % or from 10 mol % to 30 mol %. In terms of upper limits, the increased heat capacity reaction mixture may comprise less than 50 mol % heat capacity modifier(s), e.g., less than 40 mol % or less than 30 mol %. In one embodiment, a molar ratio of the heat capacity modifier(s) to ethylene in the reactant mixture is greater than 0.01:1, e.g., greater than 0.1:1, greater than 0.3:1 or greater than 0.5:1. In one embodiment water may be added to the reaction mixture. As a result, a hydrated reaction mixture is formed. In one embodiment, the hydrated reaction mixture comprises at least 0.1 mol % water, e.g., at least 1 mol % or at least 5 mol %. In terms of ranges, the hydrated reaction mixture may comprise from 0.1 mol % to 35 mol % water, e.g., from 1 mol % to 25 mol % or from 5 mol % to 20 mol %. In terms of upper limits, the hydrated reaction mixture may comprise less than 35 mol % water, e.g., less than 25 mol % or less than 20 mol %. In terms of upper limits, the hydrated reaction mixture may comprise less than 85 mol % ethylene, e.g., less than 70 mol % or less than 65 mol %.

In one embodiment, as a result of the addition of the heat capacity modifier(s), the oxygen concentration in the increased heat capacity reaction mixture, advantageously, may be increased, which provides for many benefits in process efficiency. In one embodiment, the increased heat capacity reaction mixture comprises at least 1 mol % oxygen, e.g., at least 3 mol %, at least 5 mol %, or at least 9 mol %. In terms of ranges, the increased heat capacity reaction mixture may comprise from 1 mol % to 15 mol % oxygen, e.g., from 3 mol % to 12 mol % or from 9 mol % to 12 mol %. In terms of upper limits the increased heat capacity reaction mixture may comprise less than 15 mol % oxygen, e.g., less than 12 mol % or less than 10 mol %.

In addition to heat capacity modifier(s) and oxygen, the inventive increased heat capacity reaction mixture may further comprise ethylene and acetic acid. In one embodiment, the increased heat capacity reaction mixture comprises at least 20 mol % ethylene, e.g., at least 30 mol % or at least 40 mol %. In terms of ranges, the increased heat capacity reaction mixture may comprise from 20 mol % to 70 mol % ethylene, e.g., from 30 mol % to 60 mol % or from 40 mol % to 50 mol %. In terms of upper limits the increased heat capacity reaction mixture may comprise less than 70 mol % ethylene, e.g., less than 60 mol % or less than 50 mol %. In one embodiment, the increased heat capacity reaction mixture comprises at least 1 mol % acetic acid, e.g., at least 25 mol % or at least 35 mol %. In terms of ranges, the increased heat capacity reaction mixture may comprise from 1 mol % to 85 mol % acetic acid, e.g., from 25 mol % to 75 mol % or from 35 mol % to 65 mol %. In terms of upper limits the increased heat capacity reaction mixture may comprise less than 85 mol % acetic acid, e.g., less than 75 mol % or less than 65 mol %.

Vinyl Acetate Formation

The features of the present invention may be applied to any suitable vinyl acetate production process. In other embodiments, elements of the inventive process may be employed in the production of other monomers such as, for example, acrylic acid, vinyl esters, or diacetoxyethylene.

The acetoxylation of ethylene may take place heterogeneously with the reactants being present in the gas phase. The reactor may be configured such that the reactor is capable of removing heat from the reaction. Suitable reactor types include, but are not limited to, a fixed bed reactor and a fluidized bed reactor. Preferably, the molar ratio of ethylene to acetic acid in the reaction ranges from 1:1 to 10:1, e.g., from 1:1 to 5:1; or from 2:1 to 3:1. In one embodiment, the molar ratio of ethylene to oxygen in the reaction ranges from 1:1 to 20:1, e.g., from 1.5:1 to 10:1; or from 2:1 to 5:1. In another embodiment, the molar ratio of acetic acid to oxygen in the reaction ranges from 1:1 to 10:1, e.g., from 1:1 to 5:1; or from 1:1 to 3:1.

The raw materials, e.g., acetic acid, used in connection with the process of this invention may be derived from any suitable source including natural gas, petroleum, coal, biomass, and so forth. For purposes of the present invention, acetic acid may be produced via methanol carbonylation as described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the vinyl acetate production process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, in addition to the acetic acid formed via methanol carbonylation, some additional acetic acid may be formed from the fermentation of biomass and may be used in the hydrogenation step. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. U.S. Pat. No. 5,821,111, which discloses a process for converting waste biomass through gasification into syngas, and U.S. Pat. No. 6,685,754, which discloses a method for the production of a hydrogen-containing gas composition, such as syngas including hydrogen and carbon monoxide, are incorporated herein by reference in their entireties.

The acetic acid fed to the ethylene acetoxylation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

Although carbonylation may be a preferred acetic acid production method, other suitable methods may be employed. In a preferred embodiment that employs carbonylation, the carbonylation system preferably comprises a reaction zone, which includes a reactor, a flasher and optionally a reactor recovery unit. In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

In another embodiment, the carbonylation reaction is a low water carbonylation, wherein the concentration of water maintained in the liquid reaction composition ranges from 0.1 wt. % to 14 wt. %, e.g., from 1 wt. % to 10 wt. %. The low water carbonylation may be conducted by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The disclosure of U.S. Pat. No. 5,001,259 is hereby incorporated by reference. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The ethylene also may be produced by any suitable method. In one embodiment, the ethylene is formed via the hydrogenation of acetic acid followed by the dehydration of the acetic acid to form ethylene. As another alternative, the acetic acid and the ethylene may be produced via oxidation of an alkane, e.g., ethane, as discussed in U.S. Pat. No. 6,476,261, the disclosure of which is hereby incorporated by reference. The oxygen used in the formation of vinyl acetate in the method of the present invention may further comprise other inert gases such as nitrogen. As one example, the oxygen used in the vinyl acetate reaction is provided by an air stream.

In one embodiment, additional ethylene may be fed to the reactor. This additional ethylene, as well as the reactant ethylene mentioned above, may be substantially pure. In one embodiment, the ethylene may be admixed, for example, with one or more of nitrogen, methane, carbon dioxide, carbon monoxide, hydrogen, and low levels of $C_3/C_4$ alkenes/alkanes. Additional oxygen may be fed to the reactor. The additional oxygen, if used, may be air or a gas richer or poorer in molecular oxygen than air. One suitable additional molecular oxygen-containing gas may be, oxygen diluted with a suitable diluent, for example nitrogen or carbon dioxide. Preferably, the additional molecular oxygen-containing gas is oxygen. Preferably, at least some of the oxygen is fed to the reactor independently from the ethylene and acetic acid.

The vinyl acetate reaction may suitably be carried out at a temperature in the range of from 100° C. to 300° C., e.g., from 140° C. to 225° C. or from 150° C. to 200° C. In one embodiment, the vinyl acetate reaction may be carried out at a temperature less than 300° C., e.g., less than 225° C. or less than 200° C. In another embodiment, the reaction may be carried out pressure in the range of from 0.1 MPa to 10 MPa, e.g., from 0.1 MPa to 2.5 MPa or from 1 MPa to 2.5 MPa.

Preferably, the reaction is conducted over a catalyst. Suitable catalysts include catalysts comprising a first metal and optionally one or more of a second metal, a third metal, or additional metals. The catalyst optionally comprises a catalyst support. The first and optional second and third metals may be selected from palladium, gold, boron, alkali metals, and Group IB or VIIIB transition metals. Preferred metal combinations include palladium/gold and palladium/boron.

The first metal optionally is present in an amount from 0.1 to 10 wt. %, e.g., from 0.2 to 5 wt. %, or from 0.2 to 2.5 wt. %. The additional metals, if present, may be present in amounts ranging from 0.1 to 10 wt. %, e.g., from 0.2 to 5 wt. %, or from 0.2 to 2.5 wt. %. In other embodiments, the catalyst may comprise metalloids, e.g., boron, in amounts ranging from 0.01 wt. % to 1 wt. %, e.g., from 0.01 wt. % to 0.2 wt. %. For catalysts comprising two or more metals, the two or more metals may be alloyed with one another. Alternatively, the two or more metals may comprise a non-alloyed metal solution or mixture. Also, the preferred metal ratios may vary depending on the metals used in the catalyst. If palladium and gold are utilized, the ratio may range from 0.5:1 to 20:1, e.g., from 1.8:1 to 10:1. In some exemplary embodiments where a first and second metal are used, the mole ratio of the first metal to the second metal is from 5:1 to 1:1, e.g., from 3:1 to 1:1, or from 2:1 to 1:1.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, from 1 wt. % to 8 wt. %, from 1 wt. % to 5 wt. %, or from 2 wt. % to 4 wt. %, based on the total weight of the catalyst.

Suitable support materials may include silica, alumina, silica-alumina, titania, ticano-silicates, zirconia, zircono-silicate, niobia, silicates, alumino-silicates, titanates, carbon, metals, and glasses. Preferred supports include zirconia, zircono-silicates, and titano-silicates. Suitable support modifiers may include barium, magnesium, cerium, potassium, calcium, niobium, tantalum, titanium, yttrium, strontium, zirconium, vanadium, molybdenum, and rubidium. Preferred support modifiers include niobium, titanium, magnesium, and zirconium.

Specific examples of suitable catalysts include, for example, those described in GB 1 559 5401; EP 0 330 853; EP 0 672 4563; U.S. Pat. Nos. 5,185,308; 5,691,267; 6,114, 571; 6,852,877; and 6,603,038. The disclosures of all of the above-mentioned references are hereby incorporated by reference.

GB 1 559 540 describes suitable catalysts that can be employed in the preparation of vinyl acetate by the reaction of ethylene, acetic acid and oxygen. The catalysts are comprised of: (1) a catalyst support having a particle diameter of from 3 to 7 mm and a pore volume of from about 0.2 to 1.5 ml per gram, a 10% by weight water suspension of the catalyst support having a pH from about 3.0 to 9.0, (2) a palladium-gold alloy distributed in a surface layer of the catalyst support, the surface layer extending less than 0.5 mm from the surface of the support, the palladium in the alloy being present in an amount of from about 1.5 to 5.0 grams per liter of catalyst, and the gold being present in an amount of from about 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of vinyl acetate from ethylene, acetic acid, and an oxygen-containing gas, the catalyst consisting essentially of (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

U.S. Pat. No. 5,691,267 describes a two step gold addition method for a catalyst used in the gas phase formation of vinyl acetate from the reaction of ethylene, oxygen, and acetic acid. The catalyst is formed by (1) impregnating a catalyst carrier with aqueous solutions of a water-soluble palladium salt and a first amount of a water-soluble gold compound such as sodium-palladium chloride and auric chloride, (2) fixing the precious metals on the carrier by precipitating the water-insoluble palladium and gold compounds by treatment of the impregnated carriers with a reactive basic solution such as aqueous sodium hydroxide which reacts with the palladium and gold compounds to form hydroxides of palladium and gold on the carrier surface, (3) washing with water to remove the chloride ion (or other anion), and (4) reducing all the precious metal hydroxides to free palladium and gold, wherein the improvement comprises (5) impregnating the carrier with a second amount of a water-soluble gold compound subsequent to fixing a first amount of water-soluble gold agent, and (6) fixing the second amount of a water-soluble gold compound.

U.S. Pat. No. 6,114,571 describes a catalyst for forming vinyl acetate in the gas phase from ethylene, acetic acid, and oxygen or oxygen-containing gases wherein the catalyst is comprised of palladium, gold, boron, and alkali metal compounds on a support. The catalyst is prepared by a) impregnating the support with soluble palladium and gold compounds; b) converting the soluble palladium and gold compounds on the support into insoluble compounds by means of an alkaline solution; c) reducing the insoluble palladium and gold compounds on the support by means of a reducing agent in the liquid phase; d) washing and subsequently drying the support; e) impregnating the support with a soluble alkali metal compound; and f) finally drying the support at a maximum of 1500° C., wherein boron or boron compounds are applied to the catalyst prior to the final drying.

U.S. Pat. No. 6,603,038 describes a method for producing catalysts containing metal nanoparticles on a porous support, especially for gas phase oxidation of ethylene and acetic acid to form vinyl acetate. The invention relates to a method for producing a catalyst containing one or several metals from the group of metals comprising the sub-groups Ib and VIIIb of the periodic table on porous support particles, characterized by a first step in which one or several precursors from the group of compounds of metals from sub-groups Ib and VIIIb of the periodic table is or are applied to a porous support, and a second step in which the porous, preferably nanoporous support to which at least one precursor has been applied is treated with at least one reduction agent, to obtain the metal nanoparticles produced in situ in the pores of said support.

EP 0 672 453 describes palladium-containing catalysts and their preparation for fluid bed vinyl acetate processes.

An advantage of using a palladium-containing catalyst is that any carbon monoxide produced in a prior reaction zone will be consumed in the presence of oxygen and the palladium-containing catalyst in the second reaction zone. An example of a prior reaction zone is a reaction zone for preparing the reactants. This eliminates the need for a separate carbon monoxide removal reactor.

In the ethylene acetoxylation reaction, the catalyst may have a productivity (measured in space time yield, STY) ranging from 10 g/hr-liter to 5,000 g/hr-liter, e.g., from 100 g/hr-liter to 2,000 g/hr-liter or from 200 g/hr-liter to 1,000 g/hr-liter, where g/hr-liter means grams of vinyl acetate per hour per liter of catalyst. In terms of upper limits, the space time yield maybe less than 20,000 g/hr-liter, e.g., less than 10,000 g/hr-liter or less than 5,000 g/hr-liter.

The vinyl acetate reaction may be characterized in terms of conversions based on the reactants. In one embodiment, acetic acid conversion is at least 5%, e.g., at least 15% or at least 20%. In terms of ranges, acetic acid conversion may range from 5% to 55%, e.g., from 15% to 40% or from 20% to 35%. In terms of upper limits, acetic conversion may be less than 50%, e.g., less than 40% or less than 35%. In one embodiment, oxygen conversion is at least 5%, e.g., at least 20% or at least 30%. In terms of ranges, oxygen conversion may range from 5% to 75%, e.g., from 20% to 60% or from 30% to 50%. In terms of upper limits, oxygen conversion may be less than 75%, e.g., less than 60% or less than 50%.

The composition of the crude vinyl acetate composition may vary widely depending, for example, on the reaction conditions and catalyst employed in addition to the specific scavenger(s) employed. In one embodiment, the crude vinyl acetate composition comprises from 1 mol % to 75 mol % carbon dioxide, e.g., from 5 mol % to 50 mol %, from 8 mol % to 25 mol %, or from 10 mol % to 20 mol %. In one embodiment, the crude vinyl acetate composition comprises at least 1 mol % carbon dioxide, e.g., at least 5 mol %, at least 8 mol %, or at least 10 mol %. In one embodiment, the crude vinyl acetate composition comprises less than 75 mol % carbon dioxide, e.g., less than 50 mol %, less than 25 mol % or less than 20 wt %. Some exemplary weight percentage ranges for the crude vinyl acetate composition are presented in Table 1.

TABLE 1

Crude Vinyl Acetate Compositions

| Component | Conc. (wt %) | Conc. (wt %) | Conc. (wt %) |
|---|---|---|---|
| Vinyl Acetate | 1 to 75 | 1 to 50 | 2 to 35 |
| Acetic Acid | 1 to 80 | 1 to 50 | 5 to 25 |
| Ethylene | 10 to 90 | 10 to 50 | 20 to 40 |
| Ethane | 1 to 40 | 1 to 20 | 5 to 15 |
| Water | 1 to 20 | 1 to 10 | 2 to 8 |
| Carbon Dioxide | 1 to 75 | 1 to 50 | 2 to 35 |

Process Control/Separation

Figure 1:
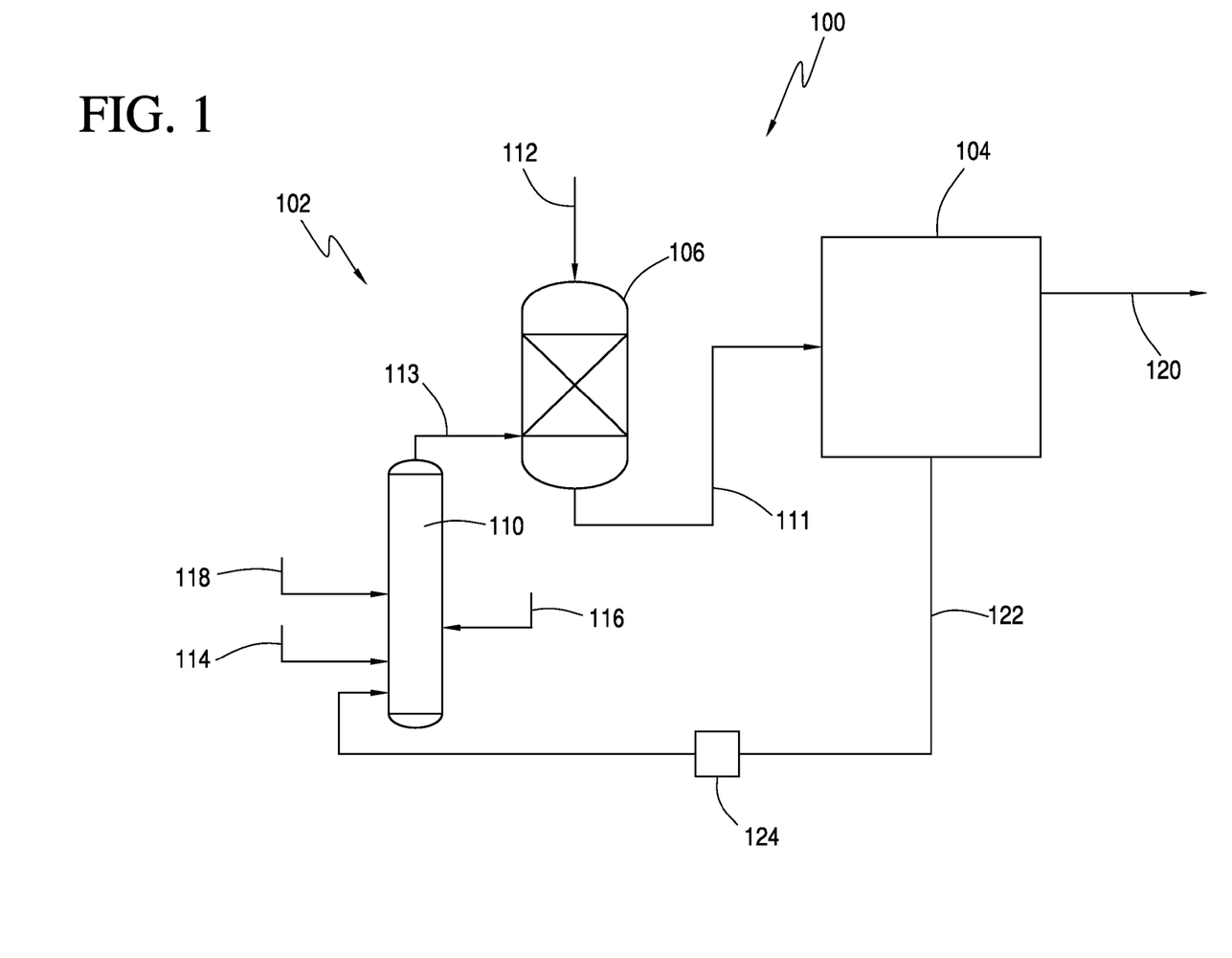
FIG. 1 is a schematic diagram of an exemplary vinyl acetate production process, which includes a reaction zone and a separation zone, in accordance with embodiments of the present invention.

In one embodiment, process control for the vinyl acetate production process is accomplished by controlling the process conditions of the reaction zone. An exemplary vinyl acetate production process 100 is shown in FIG. 1. Vinyl acetate production process 100 comprises reaction zone 102 and separation zone 104. Reaction zone 102 comprises reactor 106 and vaporizer 110. Reaction zone 102 receives the reactants, e.g., ethylene, acetic acid, and oxygen, and yields a crude vinyl acetate composition, which exits via line 111. In the embodiment shown in FIG. 1, oxygen is fed via oxygen feed 112. In another embodiment, at least a portion of the oxygen may be fed to vaporizer 110 and subsequently directed to reactor 106. As shown, acetic acid and ethylene may be fed to vaporizer 110 via acetic acid feed 114 and ethylene feed 116. In other embodiments, these reactants may be fed directly to reactor 106. In other embodiments, the reactants may be initially fed at other locations in reaction zone 102 and/or separation zone 104. In these cases, the reactant may indirectly be conveyed to vaporizer 110 and/or reactor 106. Preferably, the ethylene is fed at a point in the separation zone and the ethylene is then conveyed, via one or more separation and/or heat exchange units, to vaporizer 110. The vaporizer yields vaporized feed stream, which is directed to reactor 106 via line 113.

Reaction zone 102 also comprises heat capacity modifier feed 118, which feeds heat capacity modifier(s), indirectly via vaporizer 110, to reactor 106. In one embodiment, the heat capacity modifier(s) may be fed directly to reactor 106 (not shown). In one embodiment (not shown), the heat capacity modifier may be fed at other points in the reaction loop, e.g., make-up gas feeds, and/or at points in the carbon dioxide removal system and/or at points in the feed recovery system(s). Preferably, the heat capacity modifier is methane. The addition of the heat capacity modifier(s) to the reaction mixture provides the benefits discussed above.

Figure 2:
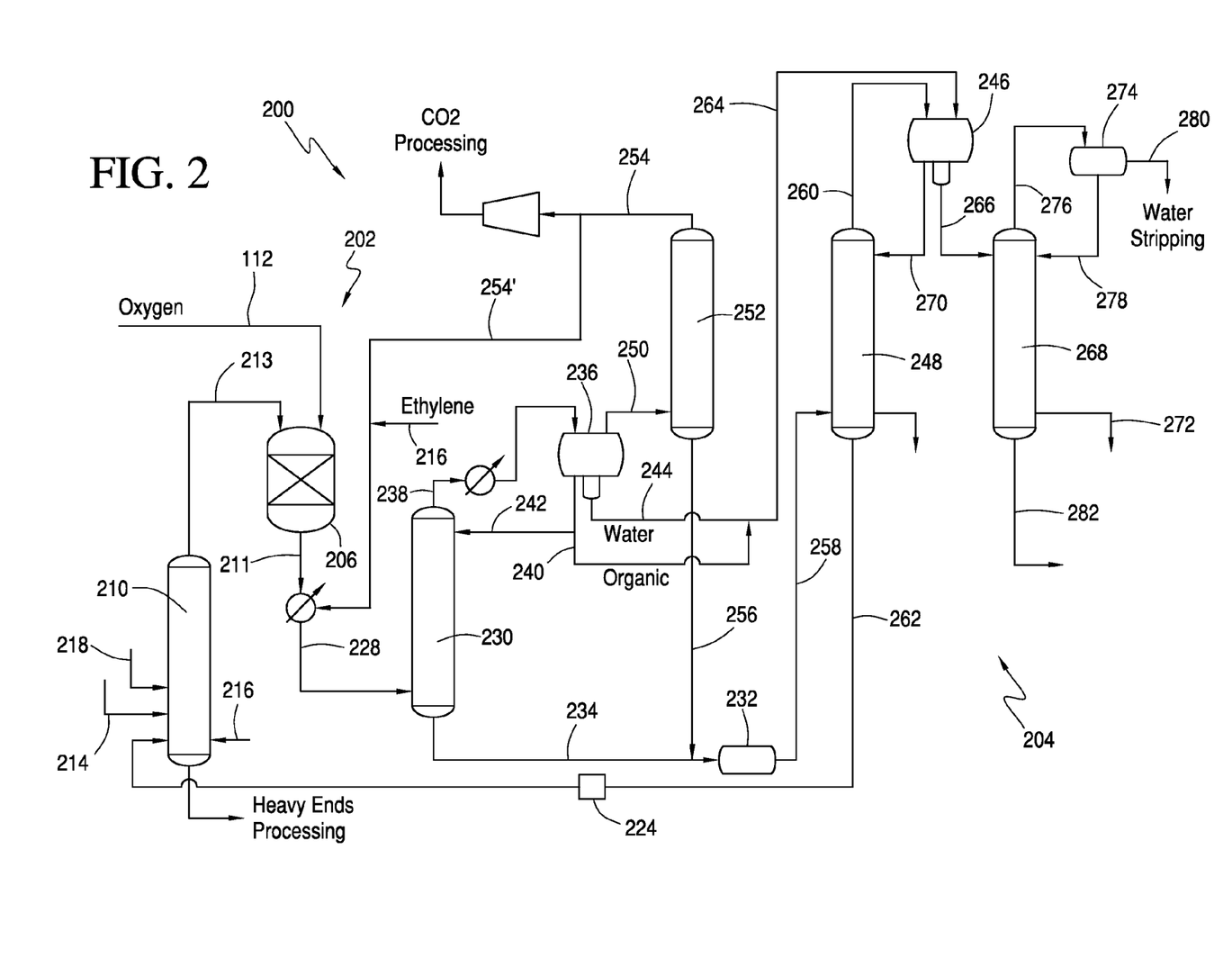
FIG. 2 is a schematic diagram of an exemplary vinyl acetate production process, which includes a reaction zone and a separation zone, in accordance with embodiments of the present invention.

Separation zone 104 may comprise any suitable separation unit or combination of separation units. Preferably, separation zone 104 comprises distillation column(s) and phase separation unit(s). An exemplary separation zone is shown in FIG. 2, which is discussed below in more detail.

Separation zone 104 receives line 111, which contains at least a portion of the crude vinyl acetate product from reactor 106. Separation zone 104 separates the crude vinyl acetate product into a purified vinyl acetate, which exits via line 120, and one or more derivative stream, which is/are represented by line 122. Separation zone 104 comprises one or more process streams, which, depending on the process stream, may comprise combinations of reactants, products, and by-products. In one embodiment, the streams include the streams entering and exiting the reactor; the streams entering and exiting the unit(s) of the separation zone; and/or from streams connecting the various units of the reaction zone or the separation zone. In some embodiments, the separation zone comprises one or more distillation columns and the one or more distillation column yield one or more derivative streams. These derivative streams may be considered process streams. Some of these derivative stream(s) comprise water and/or acetic acid.

In some embodiments, process stream samples may be collected from the various units and streams of the system. As shown in FIG. 1, analyzer 124 is configured on the derivative stream in line 122 to collects samples therefrom. Although FIG. 1 only shows analyzer 124, which is configured on the derivative stream in line 122, additional analyzers may be employed to collect sample data from the various units of the reaction zone and/or the separation zone.

Generally, changes in temperature and composition in any stream or column within the reaction system can affect other portions of the reaction system. Availability of frequent analysis of streams and columns throughout the plant can allow powerful algorithmic relationships to be developed towards optimizing reactor and purification operations. The analyzer(s) collect data relating to various parameters of the stream(s), e.g., temperature, pressure, component concentration. The analyzers may by any suitable analyzers known in the art, e.g., mass spectroscopy units, infrared, and/or near-infrared analyzers. Preferably the analyzer is an infrared analyzer.

In preferred embodiments, the collected data may be utilized to calculate the flammability limit of the reactor. Preferably, the flammability limit of the reactor is calculated based on, inter alia, the water content of the reaction mixture. As noted above, conventional vinyl acetate control processes fail to take into consideration the effects of water in the reaction mixture and the effects that this water may have on the thermodynamics of the reaction mixture, e.g., the flammability limit. In some cases, however, the water content of the vapor reaction mixture may be difficult to measure directly. It has now been discovered that, surprisingly and unexpectedly, the water content of the reaction mixture can be accurately calculated based on the water content in one or more of the derivative streams. Because the water content in the reaction mixture is accurately calculated using the water content of the derivative stream, a more accurate flammability limit, in turn, may be calculated. By providing a more accurate flammability limit calculation based on the water content of the reaction mixture, the vinyl acetate process is capable of operating at higher oxygen concentrations.

Based on the data collected by the analyzers and the calculated flammability limit, adjustments to the process may be made to establish process control and/or to operate the reactor at preferred non-flammability range that is below (or at) the calculated flammability limit. These adjustments may be made directly or indirectly. Preferably, the adjustments are made indirectly, e.g., by varying reactor temperature. For example, adjustments may be made by varying the concentration of a component in one or more of the process streams or at one or more locations in the reaction system. In a preferred embodiment, the adjustment comprises adjusting the oxygen level in the reaction mixture based on the flammability limit. For example, as an increased flammability level is calculated, the temperature of the reactor may be adjusted, which, in turn adjusts the oxygen level in the reaction mixture. As another example, the flow rate of a process stream in a connection line can be increased or decreased to vary the concentration of one or more of the components in that column or another vessel in the reaction system. Alternatively, the temperature of a process stream in a column or a reactor or the temperature profile or gradient in a column or reactor may be increased or decreased to affect the concentration of one or more components in the process stream. As another example, the concentration of a process stream component may be adjusted by direct addition or extraction of that component into or out of the process stream. In one embodiment, acetic acid concentration in the reaction system may be adjusted by increasing or decreasing the temperature of the acid tower that feeds the reactor vessel, e.g., an acid saturator. Reaction system component concentrations can be adjusted directly or indirectly by varying any number of process variables in the reaction system. Further, adjustment in one location of the reaction system may cause concentration changes at either that location or upstream or downstream of that location. For optimum process control, the measurements are transmitted to a control unit for real time analysis, and the adjustments are made almost instantly after the infrared analysis. The present invention provides a method for continuously updating the conditions of the reaction system to enhance process control in real time of the overall process to thereby optimize the production and purification of vinyl acetate product.

FIG. 2 shows an exemplary reaction/separation process. Vinyl acetate production process 200 comprises reaction zone 202 and separation zone 204. Reaction zone 202 comprises reactor 206 and vaporizer 210. Reaction zone 202 receives the reactants, e.g., ethylene, acetic acid, and oxygen, and yields a crude vinyl acetate composition, which exits via line 211. Line 211 is directed to separation zone 204. In the embodiment shown in FIG. 2, oxygen is fed via oxygen feed 212. As shown, acetic acid may be fed to vaporizer 210 via acetic acid feed 214. Ethylene may be fed, indirectly, via ethylene feed 216. These reactant feeds are exemplary and other feed suitable reactant feed schemes are well within the contemplation of the invention. The vaporizer yields vaporized feed stream, which is directed to reactor 206 via line 213. Reaction zone 202 may also comprise optional heat capacity modifier feed 218, which feeds heat capacity modifier(s), indirectly, via vaporizer 210, to reactor 206. In one embodiment, heat capacity modifier may be fed directly to the reactor (not shown).

In one embodiment, separation zone 204 provides at least one derivative of the crude vinyl acetate product in line 211. In another embodiment, the derivative stream(s) of the reactor effluent may be any stream that is yielded via the units of the separation zone. Preferably, the derivative streams are downstream of the reactor. Unreacted acetic acid in vapor form may be cooled and condensed. The remainder of the crude vinyl acetate composition in line 228, which is a derivative of the reactor effluent, is directed to predehydration column ("PDC") 230. PDC 230 separates the contents of line 228 into a residue comprising vinyl acetate and a distillate comprising vinyl acetate, water, and ethyl acetate. The distillate may further comprise light impurities. The vinyl acetate-containing residue is directed to crude tank 232 via line 234. From crude tank 232, the vinyl acetate-containing residue may be stored and/or directed to further processing.

The PDC distillate is optionally cooled, condensed, and directed to an overhead phase separation unit, e.g., decanter 236, via line 238, which is a derivative of the reactor effluent. Conditions are desirably maintained in the process such that vapor contents of line 238, once cooled, condensed, and directed to decanter 236, will separate into a light phase and a heavy phase. Generally, line 238 is cooled to a temperature sufficient to condense and separate the condensable components, e.g., vinyl acetate, water, acetic acid, and other carbonyl components, into an aqueous phase and an organic phase. The organic phase exits decanter 236 via line 240. A portion of the organic phase may be refluxed back to PDC 230, as shown by stream 242, which is a derivative stream. The aqueous phase exits decanter 236 and is directed via line 244 to further separation processing. As an example, line 244 may be directed to decanter 246 of an azeotrope column 248. Lines 240 and 244 optionally may be combined, as shown, and directed to decanter 246 of azeotrope column 248.

Stream 238 may include carbon monoxide, carbon dioxide, ethylene, ethane and other noncondensable gases, which may be directed via stream 250 from decanter 236 to scrubber 252. Scrubber 252 removes, inter alta, carbon monoxide, carbon dioxide, and hydrocarbons such as ethylene and ethane from stream 250. The separated noncondensable components may be conveyed to further processing, e.g., carbon dioxide removal, as shown by stream 254. In another embodiment, at least a portion of stream 254 is recycled bad to the reactor effluent or to heat exchange equipment downstream of reactor 206, as shown by stream 254'. The residue exiting scrubber 252 comprises vinyl acetate, water, and acetic acid. The residue exits scrubber 252 via line 256 and may be combined with the vinyl acetate from line 234 prior to being directed to crude tank 232.

From crude tank 232, the vinyl acetate is directed to azeotrope column 248 via line 258, which is a derivative stream. Azeotrope column 248 separates line 258, which comprises vinyl acetate, acetic acid, and water, into a distillate stream in line 260 and a residue stream 262. Decanter 246 at the top of azeotrope column 248 receives line 264, which comprises the aqueous and/or organic phases from decanter 236. In addition, decanter 246 receives the distillate from azeotrope column 248. Azeotrope column 248 separates line 258, which comprises vinyl acetate, acetic acid, and water. The residue from azeotrope column 248 comprises acetic acid and water. This stream may be recycled back to vaporizer 210 via line 262, or may be conveyed directly to reactor 206 (not shown).

In preferred embodiments, analyzer 224 is configured on line 262 to measure the water content in the azeotrope column residue. It has now been discovered that, surprisingly, the water content in the azeotrope column residue is closely related to the water content in the reaction mixture. As such, the water content in the azeotrope column residue may be employed in a mathematical formula to more accurately calculate the flammability. In one embodiment, the water content in this derivative stream, e.g., the azeotrope column residue, is measured via an infrared analyzer. In one preferred embodiment, the residue in line 262 may be collected in a buffer tank (not shown). In one embodiment, the measurement of the water content of the azeotrope column residue is performed in the buffer tank. As discussed above, in some embodiments, the measurement of the water in the reaction mixture stream may be taken directly from the reaction mixture feed.

The distillate from azeotrope column 248 comprises vinyl acetate and water and is directed to decanter 246, e.g., a reflux decanter, via line 260. Decanter 246 separates at least a portion of streams 260 and/or 264 into aqueous and organic phases. The organic phase, which comprises vinyl acetate, exits decanter 246 via line 266, which is a derivative of the reactor effluent, and is directed to further processing. As one example, line 266 is directed to dehydration column 268. The aqueous phase exits decanter 246 via line 270. Line 270 (or a portion thereof) may be refluxed back to azeotrope column 248.

Dehydration column 268 removes additional water from the contents of line 266, thus yielding purified vinyl acetate via line 272. The water-containing distillate of dehydration column 268 may be directed to overhead tank 274 via line 276. From overhead tank 274, line 278, which contains an amount of vinyl acetate, may be returned to dehydration column 268. Line 280, which comprises water and impurities may be directed to further processing, e.g., water stripping. The residue of dehydration column 268 exits via line 282. The residue comprises various residuals, which may be recycled or otherwise disposed.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for forming vinyl acetate, comprising the steps of:
    (a) providing a reaction mixture having an initial heat capacity and comprising acetic acid, oxygen, ethylene, and optionally water;
    (b) adding to the reaction mixture at least one heat capacity modifier selected from the group consisting of nitrogen, methane, ethane, carbon dioxide, and mixtures thereof to form an increased heat capacity reaction mixture; and
    (c) contacting the acetic acid, oxygen, and ethylene over a catalyst under conditions effective to form a crude vinyl acetate product comprising vinyl acetate, water, and from 8 mol % to 25 mol % carbon dioxide.

2. The process of claim 1, wherein the at least one heat capacity modifier is selected from the group consisting of nitrogen, water, carbon dioxide, ethane, methane, and combinations thereof.

3. The process of claim 1, wherein the increased heat capacity reaction mixture comprises at least 1 mol % of the at least one heat capacity modifier.

4. The process of claim 1, wherein the molar ratio of the at least one heat capacity modifier to ethylene in the reaction mixture from step (b) is greater than 0.01:1.

5. The process of claim 1, wherein the reaction mixture from step (b) comprises at least 1 mol % oxygen.

6. A process for forming vinyl acetate, comprising the steps of:
    (a) contacting acetic acid, oxygen, ethylene in the presence of water and over a catalyst under conditions effective to form a crude vinyl acetate product comprising vinyl acetate and water;
    (b) forming from the crude vinyl acetate product a derivative stream comprising acetic acid and water and having a composition different from the crude vinyl acetate product
    (c) calculating the flammability limit based on water content in the reaction mixture;
    (d) adjusting reaction parameters based on the flammability limit,
    wherein the water content in the reaction mixture is calculated based on water content of the derivative stream.

7. The process of claim 6, wherein the derivative stream is a residue of a distillation column.

8. The process of claim 6, wherein the water content in the derivative stream is measured via an infrared analyzer.

9. The process of claim 8, wherein the derivative stream is collected in a buffer tank and the measuring is performed downstream of the buffer tank.

10. The process of claim 6, wherein step (c) comprises: adjusting the oxygen level in the reaction mixture based on the flammability limit.

11. The process of claim 10, wherein the adjusting comprises adjusting the reactor temperature to adjust the oxygen level in the reaction mixture.

12. The process of claim 6, wherein step (a) forms carbon dioxide and wherein the crude vinyl acetate product further comprises from 1 mol % to 75 mol % carbon dioxide.

13. A process for forming vinyl acetate, comprising the step of reacting acetic acid, oxygen, and ethylene in the presence of water and a catalyst under conditions effective to form a crude vinyl acetate product comprising vinyl acetate and from 8 mol % to 25 mol % carbon dioxide, wherein the combined reactants comprise at least 1 mol % of at least one heat capacity modifier selected from the group consisting of nitrogen, methane, ethane, carbon dioxide, and mixtures thereof and from 20 mol % to 70 mol % ethylene.

14. The process of claim 13, further comprising the step of adding additional water to the combined reactants to form a hydrated reaction mixture.

15. The process of claim 14, wherein the hydrated reaction mixture comprises at least 0.1 mol % water and less than 85 mol % ethylene.

16. A process for forming vinyl acetate, comprising the steps of:
    (a) reacting a reaction mixture comprising acetic acid, oxygen, ethylene, and at least 1 mol % methane in the presence of water and a catalyst under conditions effective to form a crude vinyl acetate product comprising vinyl acetate, wherein the reaction mixture comprises at least 1 mol % oxygen and from 20 mol % to 70 mol % ethylene;
    (b) calculating a flammability limit of oxygen based on the amount of water in the reacting step;
    (c) forming a derivative stream comprising acetic acid and water and having a composition different from the crude vinyl acetate product from the crude vinyl acetate stream;
    (d) measuring the water content in the derivative stream via an infrared analyzer;
    (e) calculating the amount of water in the reacting step based on the water content of the derivative stream;
    (f) adjusting the reaction temperature to adjust the amount of oxygen in the reaction mixture based on the calculated flammability limit.

* * * * *